United States Patent [19]

Bevilacqua

[11] 4,196,737
[45] Apr. 8, 1980

[54] TRANSCUTANEOUS ELECTRODE CONSTRUCTION

[75] Inventor: Albert J. Bevilacqua, Downers Grove, Ill.

[73] Assignee: C. R. Bard, Inc., Murray Hill, N.J.

[21] Appl. No.: 898,650

[22] Filed: Apr. 21, 1978

[51] Int. Cl.$^2$ .............................................. A61N 1/04
[52] U.S. Cl. ..................................... 128/798; 128/802
[58] Field of Search ............... 128/417, 418, 416, 404, 128/410, 411, 2.06 E, 2.1 E, 303.13, DIG. 4, 798, 802, 803, 783, 639, 640, 641, 644

[56] References Cited

U.S. PATENT DOCUMENTS

| | | | |
|---|---|---|---|
| 3,610,229 | 10/1971 | Zenkich | 128/2.06 E |
| 3,817,252 | 6/1974 | Maurer | 128/416 |
| 3,828,766 | 8/1974 | Krasnow | 128/2.1 E |
| 3,848,600 | 11/1974 | Patrick, Jr. et al. | 128/303.13 |
| 3,862,633 | 1/1975 | Allison et al. | 128/2.06 E |
| 3,865,099 | 2/1975 | Robichaud | 128/2.1 E |
| 3,868,946 | 3/1975 | Hurley | 128/2.1 E |
| 3,945,384 | 3/1976 | Allison et al. | 128/2.06 E |
| 3,972,329 | 8/1976 | Kaufman | 128/2.06 E |
| 3,989,035 | 11/1976 | Zuehlsdorff | 128/2.1 E |
| 4,117,846 | 10/1978 | Williams | 128/417 X |

FOREIGN PATENT DOCUMENTS

675494 12/1963 Canada ..................................... 128/417

*Primary Examiner*—Lee S. Cohen
*Attorney, Agent, or Firm*—Trexler, Wolters, Bushnell & Fosse, Ltd.

[57] ABSTRACT

There is disclosed a transcutaneous electrode construction for the application of electrical pulses to a patient, such as might be employed in pain therapy. The electrode construction includes a base member comprising a sheet of nonconductive material having an adhesive coating on one surface. A thin liquid impervious nonconductive sheet of smaller surface area than the base member is centrally affixed thereto on the adhesive coated surface so as to be entirely surrounded by the adhesive coating. A sponge pad overlies the liquid impervious sheet and has a larger surface area than the liquid impervious sheet so that its peripheral edges engage and adhere to the adhesive of the base member while leaving sufficient adhesive surface exposed for adhering to the skin of the patient. Due to the fact that the sponge pad is adhered to the base member only about the edges thereof, a chamber or pocket is formed between the sponge pad and the impervious sheet for receiving a quantity of electrolytic gel. A liquid impervious cover member is releasably affixed to the exposed adhesive coating surface of the base member, to overlie and protect the electrode, and particularly the adhesive coating and the sponge pad and gel filled pocket or chamber. When use of the electrode is desired, the electrode may be removed from the cover member and the cover member discarded.

6 Claims, 3 Drawing Figures

U.S. Patent    Apr. 8, 1980    4,196,737

TRANSCUTANEOUS ELECTRODE CONSTRUCTION

BACKGROUND OF THE INVENTION

This invention relates generally to a transcutaneous electrode design, and more particularly to a novel transcutaneous electrode construction which facilitates the retention of the electrolytic gel and is useful in application of electrical stimulus to nerve tissue, as for example, might be utilized in pain therapy.

In recent years, utilization of electrical nerve stimulus in pain therapy has become increasingly wide spread and accepted as a therapeutic practice. In theory, the applied electrical stimulus results in an "overload" condition of the associated nerve tissues and structures so that a pain stimulus existing on these nerve tissues or structures cannot be transmitted to the brain to produce the normal pain response in the patient. In this regard, the physician or therapist will utilize suitable electrodes connected with a source of electrical current to effect the desired nerve stimulation. However, it will be appreciated that the construction as well as the appearance of conventional metallic electrodes and the like may cause undue alarm to the patient, as well as being relatively inconvenient to handle by the physician or therapist.

The apparatus and procedure utilized generally in pain therapy require that the electrode or electrodes be affixed to the patient's skin adjacent the nerves to be stimulated by use of an adhesive or the like. Also, of importance is the fact that a substantial quantity of electrolytic gel or past material must be employed to assure proper conductive contact with the patient's skin. While prior electrode designs have been used in this type of treatment, they have not proven satisfactory. More specifically, the prior art electrode constructions were developed primarily for the monitoring of biomedical functions, i.e. ECG's, or for use in electro-surgery, typical examples of which are shown in U.S. Pat. Nos. 3,989,035 and 3,805,796. These prior electrode designs proved unsatisfactory in that they were not able to store or accommodate the necessary or desired quantity of electrolytic gel required for pain therapy use. While these designs employed gel pads formed of a sponge-like material, the quantity of gel that could be stored was limited to that which could be absorbed by the gel pad. If a larger quantity was used, a major portion of the gel was disposed on the exterior of the pad and problems arose upon application of the electrode. In this regard, as the electrode was applied the gel would tend to be squeezed or flow along the interface of the base with the patient's skin, thus preventing proper attachment of the electrode. As will become clear from the discussion to follow, the present invention provides an improved design which is able to accommodate the larger gel quantities needed with transcutaneous electrodes.

In addition to the above-mentioned prior art electrodes, designs have been proposed, which utilize a formed plastic base section that provides a recess for the gel; see U.S. Pat. Nos. 3,862,633; 3,945,384; and 3,865,099. These designs, however, require the molding or vacuum forming of the base section, and are thus expensive to fabricate and assemble.

With the above in mind, it should be noted that the present invention employs a design wherein the electrode is fabricated primarily from sheet material and as such can be manufactured using automated machinery. The advantage of economy of construction and automated manufacture are achieved without relinquishing the advantages of a gel chamber, and this is attained by providing that the gel pad is adhered to the adhesive on the base layer only at is edges. As such, the major portion of the gel pad, which overlied the nonconductive layer, is not affixed to the underlying structure. Accordingly, the gel pad and nonconductive layer serve to define a chamber or pocket, into which a large quantity of gel may be injected and stored. Upon use of the electrode, while the gel can pass through the porous gel pad, and will thoroughly soak the pad, the electrode can be adhered to the patient's skin without the squeezing or migration of gel along the skin interface. Thus, the electrolytic gel is maintained in the area of the gel pad, and is preferred for the efficient and proper operation of the electrode.

Other objects, features and advantages of the present invention will become more readily apparent from the following detailed description of the illustrated embodiment which is presented in conjuction with the accompanying drawings.

DETAILED DESCRIPTION OF THE ILLUSTRATED EMBODIMENT

Figure 1:
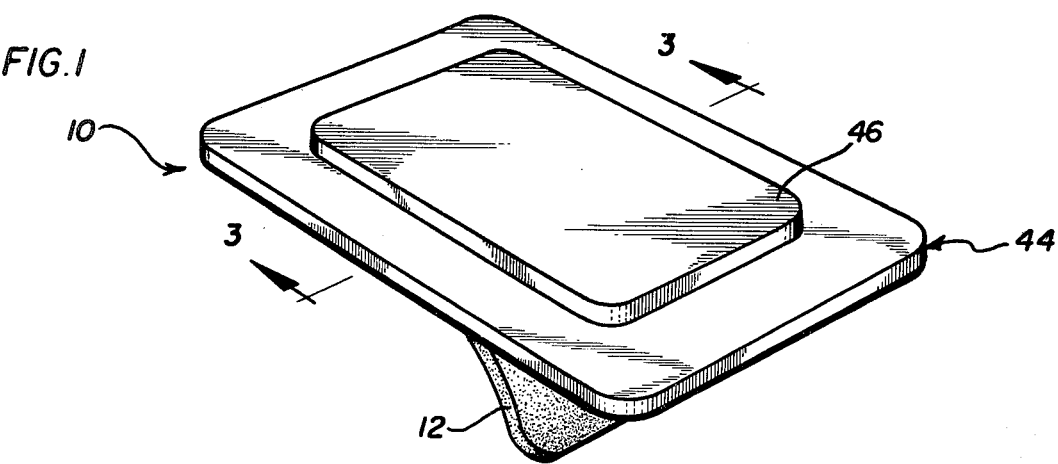
FIG. 1 is a perspective view of an electrode constructed in accordance with the present invention, with a protective cover member overlying a major portion thereof.
Figure 2:
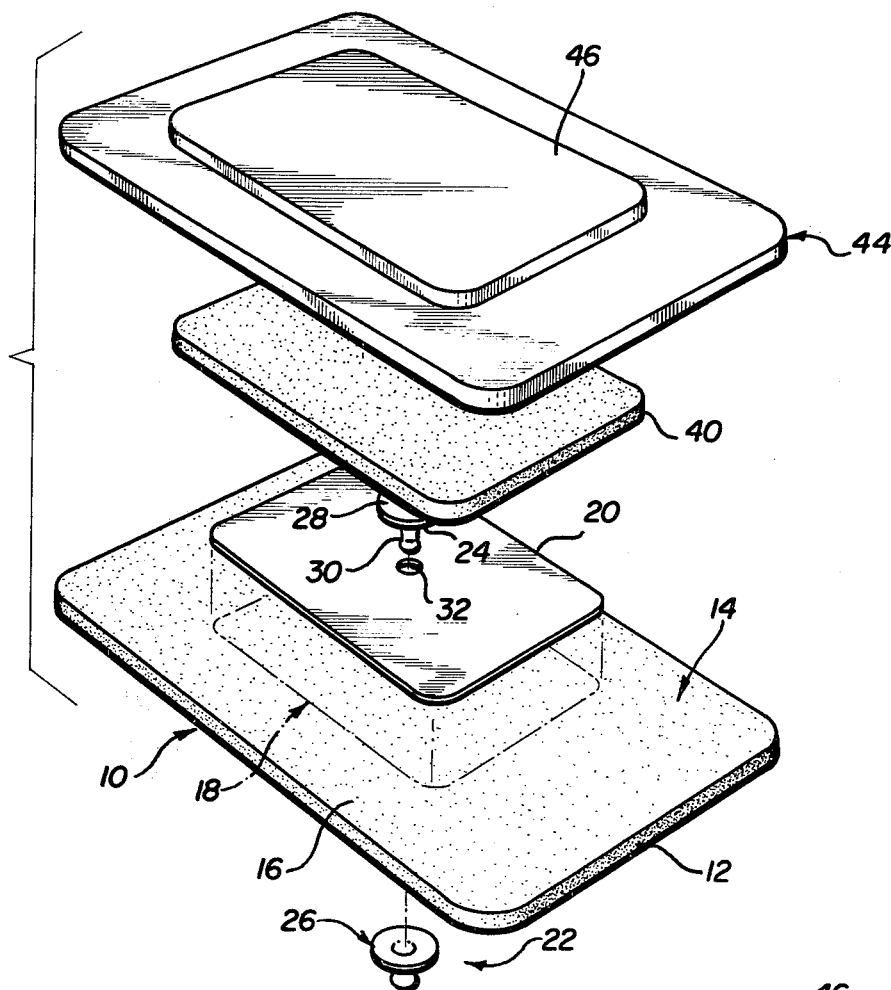
FIG. 2 is an exploded perspective view of the electrode and cover of FIG. 1.
Figure 3:
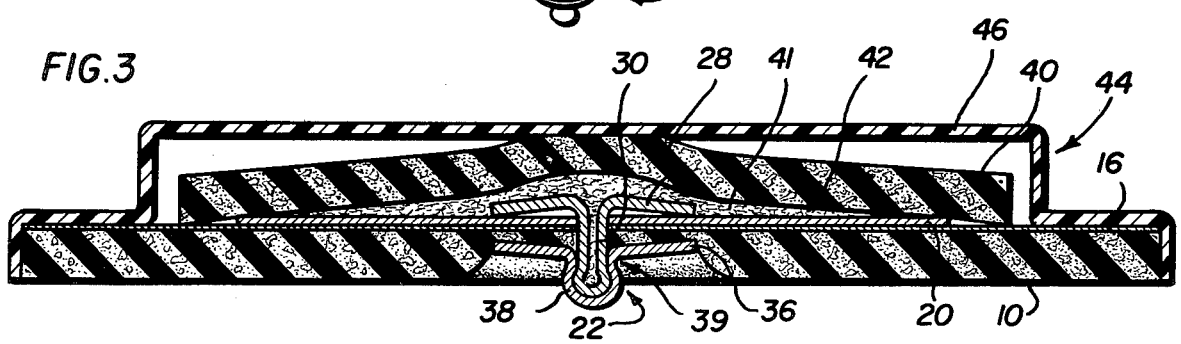
FIG. 3 is an enlarged sectional view taken generally along the line 3—3 of FIG. 1, wherein some of the dimensions have been exaggerated slightly to illustrate certain features of the invention.

Referring now in detail to the drawings, a transcutaneous electrode construction in accordance with the present invention is shown in FIGS. 1–3 and designated generally by reference numeral 10. The electrode 10 includes a base pad or layer 12 formed from a flexible sheet of nonconductive material such as a foam-like cellular plastic material of the type generally known as polyethelene or polyurethane. This material, if desired, may be moisture impervious, or can be of a "breathable" foam, both of which are known in the art. The upper surface 14 of the base pad or sheet 12 is covered with an adhesive substance 16. The adhesive substance 16 is effectively neutralized or de-activated in an area designated generally 18, substantially centrally located on the surface 14 of the base pad or sheet 12. In the illustrated embodiment, this is accomplished by the application thereto of a relatively thin, flexible sheet of moisture impervious nonconductive material 20, which is substantially smaller in area than the surface 14 of the base member or sheet 12. Accordingly, an area of the adhesive 16 is maintained active and intact, which area substantially surrounds the sheet 20.

In the illustrated embodiment, the adhesive 16 in the area 18 is deactivated by the use of the sheet 20, which also provides a moisture barrier against migration of the gel into the foam base sheet 12. This is important where a "breathable" or porous foam material is employed for the base 12, and extended shelf life is desired. Should the foam sheet 12 be constructed of a non-porous, moisture impervious material, the area 18 can be deactivated by sheet 20, or the use of some other means; as for example, an adhesive deactivating agent, many of which are known in the art, may be applied to the area 18, or the adhesive 16 may be applied in a pattern which leaves the area 18 free of adhesive.

A terminal assembly designated generally 22 is carried by the base sheet 12 and in the illustrated embodiment, the terminal assembly 22 is in the form of a snap type fastener, and is best illustrated in FIG. 3. The assembly 22 includes an inner element or stud 24 and an outer element or eyelet 26 engageable over the stud 24. The inner stud 24 includes a flange or skirt portion 28 and a post portion 30 which extends through an aperture 32 formed through both base 12 and the sheet 20. The outer element or eyelet 26 includes a similar flange or skirt portion 36 and a socket portion 38 for receiving the post 30 in engagement therewith, with the socket 38 being deformed slightly at 39 to maintain assembly. Consequently, it will be seen that the terminal member engages the sheets 12 and 20 at the respective flange or skirt members 28 and 36. The outer element 26 provides a convenient terminal member at the opposite sides of the base sheet or layer 12 for attachement of wires or leads from an external current source (not shown).

A sponge-like gel pad or member 40 affixed to the base 12, and overlies the sheet 20. In accordance with a feature of the invention, the sponge or gel pad 40 comprises a relatively thin sheet of liquid absorbent, cellular sponge material of an area somewhat greater than that of the sheet 20 but substantially less than the area of the base pad 12. Accordingly, it will be seen that the sponge or gel pad 40 is adhered to the adhesive material 16 about its peripheral edge portions and completely surrounds the nonconductive sheet member 20, while leaving a substantial portion of the adhesive material 16 exposed and active for attachment of the electrode 10 to the skin of the patient. Advantageously, as best viewed in FIG. 2, the major portion of pad 40 is not affixed to the underlying structure, due to the deactivating of the adhesive 16 by sheet 20. As such, the sheet 20 cooperates with the gel pad 40 to define a chamber or pocket 42.

During assembly of the electrode 10 a quantity of electrolytic or conductive gel 41 is injected through the pad 40 into the chamber 42, with the sheet 20 serving in effect as a bottom wall for said pocket or chamber 42. Various suitable electrolytic or conductive gels are readily available and well known to those in the art. It will be noted that the chamber or pocket 42 has been exaggerated in height somewhat in FIG. 3, to facilitate a clear showing thereof.

In addition to the above structure, the entire top surface of the electrode is protected by a cover structure 44. The cover structure 44 of the illustrated embodiment includes a flexible sheet of non-porous, liquid impervious material which overlies the surface 14 and adjacent sides of the base sheet or pad 12. The material of the cover member 44 is such that while it will adhere to the adhesive 16, it can be removed easily immediately prior to use of the electrode 10, without damaging or altering the adhesive material 16. Suitable materials or coatings for this purpose are well known in the art. The cover member 44 further includes a raised or cup-like central portion 46 which generally overlies and protects the sponge member 40. Accordingly, the cover member 44 and cup-like portion 46 prevents undesired compression of the sponge 40 and effectively seals the electrode construction 10, thus avoiding evaporation or migration of the electrode gel material 41 during storage. As such, the protective cover member 44 assures a relatively long shelf life of the electrode 10. As best seen in FIG. 1, the cover member 44 may be easily removed by "peeling back" an edge, immediately prior to using the electrode 10.

As will be apparent from the foregoing discussion, certain dimensional features of the electrode construction are thus significant in obtaining the desired advantages. In this regard, however, it is not intended to imply nor is it practical to state exact limits or relative dimensions of the several members. On the contrary, the nature and interelation of these dimensions may vary depending upon the use to which the electrodes are put and the quantity of electrolytic gel employed. What is significant in this regard, however, is that the gel receiving pocket or chamber 42 be of sufficient volume or dimension to accept a desired quantity of electrolytic gel. This quantity of gel is chosen so that upon application of electrode to the patient's skin, the gel will not be squeezed into the interface of the adhesive coated surface 14 and the patient's skin, but will nonetheless saturate the sponge 40 so as to assure electrical conduction. It will be appreciated that the absorptive qualities of the sponge and its relative volume must also be taken into consideration in this regard, in providing a suitable electrode structure 10 for a particular application.

In use the protective cover member 44 is first removed or peeled away from the surface 14 of the electrode 10, exposing the adhesive 16 and the sponge 40. The electrode 10 is then attached to the patient by firmly pressing the surface 14 to adhere to the skin about the area to be treated. As mentioned, the pocket or chamber 42 retains a substantial quantity of the gel 41 interiorly of the gel pad 40, so as to permit attainment of adhesive engagement and electrically conductive contact without squeezing of the electrolytic gel along the interface of the base surface 14 with the patient's skin. Accordingly, upon proper attachment of the gel-saturated sponge member 40 will be slightly compressed and in surface contact engagement with the patient's skin. This, then completes an electrical circuit via the gel-saturated sponge 40, and the terminal member 22, with the source of electrical current.

While a preferred embodiment of the present invention has been illustrated and described herein, various changes and modifications may occur to those skilled in the art and possessed of this disclosure. Such changes and modifications are to be understood as forming a part of the present invention, insofar as they fall within the spirit and scope of the appended claims.

The invention is claimed as follows:

1. An electrode construction for transcutaneous application, such as might be employed in electrical stimulation of nerves, said electrode construction comprising: a base member comprising a flexible sheet of nonconductive material and having one surface thereof adhesively coated for adhering to the skin of a patient and defining a predetermined surface area, a relatively thin liquid impervious nonconductive sheet of a predetermined surface area substantially less than said predetermined surface area of said base member and affixed to said adhesive coated surface so as to leave a substantial portion of said surface completely surrounding said liquid impervious sheet, a sponge member overlying said liquid impervious sheet, and a conductive electrode having a peripheral portion between said impervious sheet and said sponge member and a portion extending substantially centrally through said base member and said impervious sheet to form a terminal for receiving an electrical conductor, said sponge member defining a surface area greater than the surface area of said impervious sheet, substantially greater than the surface area of said electrode peripheral portion and less than the surface area of said base member and adhered to said base member about the peripheral edge portions of said sponge member substantially distant from said electrode peripheral portion so as to substantially overlie and surround said impervious sheet and form a pocket therewith for receiving a quantity of electrolytic gel and said impervious sheet further preventing migration of said electrolytic gel into said base member.

2. An electrode construction according to claim 1 wherein said sponge member comprises a relatively flat sheet of liquid absorbing sponge material.

3. An electrode construction according to claim 2 further including a liquid impervious cover structure overlying said sponge member, and removably adhering to the surrounding adhesive-coated surface of said base member, so as to form a removable protective cover for said electrode construction.

4. An electrode construction according to claim 1 wherein said conductive electrode comprises a snap-type fastener including an inner element which includes said peripheral portion and an outer element engaged through said impervious sheet and said base member, the inner element providing electrical contact with the electrolytic gel adapted to be introduced into said pocket and said outer element providing external terminal means for connecting said electrode construction to an external source of electrical current.

5. An electrode construction for application to the skin of a patient, said construction comprising: a base member formed from a nonconductive material having an adhesive coating on one surface thereof for attachment of the electrode to the skin of a patient, a liquid impervious relatively thin sheet of nonconductive material adhered to said one surface of the base member and having an area substantially less than the area of said one surface and substantially centrally disposed thereover; a sponge pad overlying said impervious sheet and having a peripheral edge portion thereof engaged with and adhered to said base member to define with said impervious sheet a pocket therebetween for receiving a quantity of electrolytic gel, with said sponge pad being surrounded by at least a portion of said base member adhesive coated surface and said impervious sheet precluding migration of the electrolytic gel into said base member; and terminal means carried by said base member for electrical contact between said electrolytic gel and the side of said base member opposite said adhesive coated surface, to form a terminal for connection of said electrode to a current generating device.

6. An electrode construction according to claim 5 further including a liquid impervious cover structure having a central raised portion overlying said sponge pad, and removably adhered to said base member, so as to prevent undesired compression of said sponge pad and seal the electrode construction against evaporation or migration of said electrolytic gel, during storage of said electrode construction.

* * * * *